United States Patent
Zawitz

(10) Patent No.: US 7,601,045 B2
(45) Date of Patent: Oct. 13, 2009

(54) THERAPEUTIC HAND TOYS

(75) Inventor: Richard E. Zawitz, San Francisco, CA (US)

(73) Assignee: Tangle, Inc., South San Francisco, CA (US)

(*) Notice: Subject to any disclaimer, the term of this patent is extended or adjusted under 35 U.S.C. 154(b) by 45 days.

(21) Appl. No.: 11/015,387

(22) Filed: Dec. 16, 2004

(65) Prior Publication Data

US 2006/0014468 A1    Jan. 19, 2006

Related U.S. Application Data

(60) Provisional application No. 60/588,650, filed on Jul. 16, 2004.

(51) Int. Cl.
*A63H 33/04* (2006.01)
(52) U.S. Cl. .................. 446/102; 446/487; 446/121
(58) Field of Classification Search .............. 446/102, 446/85, 92, 121; 63/3, 10, 41
See application file for complete search history.

(56) References Cited

U.S. PATENT DOCUMENTS

| 3,422,565 | A | * | 1/1969 | Dreyfuss et. al. | 446/102 |
| 3,597,858 | A | * | 8/1971 | Ogsbury et al. | 446/115 |
| 3,706,158 | A | * | 12/1972 | Jensen | 446/92 |
| 3,900,984 | A | * | 8/1975 | Garelick, Herbert J. | 446/486 |
| 4,232,473 | A | * | 11/1980 | Jenkins | 446/102 |
| 4,362,031 | A | * | 12/1982 | Obermuller | 63/15 |
| 4,509,929 | A | | 4/1985 | Zawitz | |
| 4,753,086 | A | * | 6/1988 | Schmidt | 63/3 |
| 4,929,211 | A | * | 5/1990 | Resnick et al. | 446/14 |
| 5,110,315 | A | | 5/1992 | Zawitz | |
| 5,918,373 | A | | 7/1999 | Cummings | |
| 5,964,634 | A | * | 10/1999 | Chang | 446/85 |
| 6,086,445 | A | | 7/2000 | Zawitz | |
| 6,461,215 | B1 | * | 10/2002 | Kunz et al. | 446/107 |
| 6,676,474 | B2 | | 1/2004 | Glickman | |

OTHER PUBLICATIONS

U.S. Appl. No. 10/744,962, filed Dec. 23, 2003, Zawitz

* cited by examiner

*Primary Examiner*—Gene Kim
*Assistant Examiner*—Urszula M Cegielnik
(74) *Attorney, Agent, or Firm*—Townsend and Townsend and Crew LLP

(57) ABSTRACT

The invention provides systems and methods for a textured therapeutic toy that can be manipulated into an infinite number of shapes and configurations. The invention is best applied to relieve minor stress as well as strengthen hand muscles, rehabilitate finger and joint movement and improve overall range of hand motion. In one exemplary embodiment, a textured coating is applied to the surface of each segment that gives the therapeutic toy a unique feel, thereby creating a pleasant sensation and feel to the hands and fingers.

13 Claims, 16 Drawing Sheets

THERAPEUTIC HAND TOYS

CROSS REFERENCES TO RELATED APPLICATIONS

This application claims the benefit of U.S. Provisional Patent Application No. 60/588,650, filed Jul. 16, 2004, the complete disclosure of which is herein incorporated by reference.

BACKGROUND OF THE INVENTION

This invention relates generally to a toy formed by a plurality of pivotally connected segments, and more particularly to a therapeutic hand toy that may be twisted into an infinite variety of useful and decorative structures.

Stresses, injuries and health issues are an everyday part of life. In today's fast-paced, hectic world, stress-related illnesses and injuries are more prevalent than the common cold. We all face it, but how we deal with it makes the difference between being healthy and being sick.

The hands are particularly sensitive to the many stresses associated with daily life. However, the hands are also a major source of stress relief. Aromatherapy lotions, hand massages and squishy stress relief figures assist in relieving overall stress and may provide a small degree of strengthening and conditioning to the hand, fingers and joints.

In addition to stress, people with musculoskeletal impairment of the hand and wrist are subject to loss of basic manipulative functions essential to carrying out daily activities. Such a loss can be disheartening, debilitating and sometimes incapacitating since it may lead to the reliance on the assistance and care from others. Studies have shown that clinically controlled exercise is important for restoring or maintaining hand function. While it is possible to motivate patients in a clinical environment to do hand exercises, long-term post-clinical enforcement of a therapeutic program is rarely achieved.

Hence, there is a need for a therapeutic toy that is manipulated by the hand and fingers for improving and rehabilitating hand and finger muscle performance, restoring joint and range of hand motion while at the same time providing both stress relief and hours of enjoyment. It is desirable to provide such a therapeutic hand toy that may be manipulated between the fingers and the palm to provide relief from daily stresses as well as strengthening and conditioning for rehabilitating and preventing minor injuries to the hand, fingers and wrist. Such a toy would provide hours of enjoyment and therapeutic aid by keeping the brain engaged, stimulated and interested in a textured toy that can be twisted into a multitude of patterns, shapes and textures.

BRIEF SUMMARY OF THE INVENTION

In a broad sense, the invention provides various toys that may be manipulated with one or both hands. The toys are constructed of multiple segments or links that are connected and may be twisted or turned relative to each other. An important aspect of the invention is the therapeutic benefits provided by the toys. Such benefits include, but are in no way limited to, helping strengthen or rehabilitate the fingers, hands, or forearms, as well as relieving stress and providing relaxation, among others.

To provide such benefits, the toy segments may be provided with a wide variety of therapeutic elements. Such therapeutic elements may include resilient coatings, rotatable or slidable elements on the surface of the segments, heating or cooling of the segments, vibratable elements, encased gels or liquids, various textured surfaces, colors and/or lights, varying sizes, thicknesses and/or levels of resilience, therapeutic magnets, surfaces that move up and down or in and out, various natural or synthetic materials, such as fabrics, leather, features, fibers, seeds, other plants and the like, scented materials, herbs, flavored materials, sticky surfaces, raised or lowered images (including brail), lotions, ointments, medicines, lubricants, sponges, porous materials, foams, rubbers, bendable tabs, extensions, spikes, clays or putty, electrical stimulation elements, and the like.

In one specific embodiment, the invention provides both methods and apparatus for a texture coated therapeutic tool for hand, mind and overall wellness of being. The applications for such a textured twisting stress reliever are many, ranging from recreation for children and adults to strengthening and rehabilitation for individuals with therapeutic needs. The texture coating on the therapeutic hand toy is soothing and gentle to the touch, providing the user an improved feel over typical non-coated materials such as plastic. As a result, the therapeutic value of the toy is enhanced due to an increase in the length of time the toy is used. Hence, the hand tools of the invention may be used to assist with a variety of ailments, such as smoking cessation or other habits, to assist those suffering from hand ailments, such as arthritis, carpel tunnel syndrome, and the like, and to assist with developing muscle tone in the hand, among others.

In one particular aspect, the therapeutic twisting hand toy has a plurality of serially connected segments having a first end pivotally secured to one of two adjacent segments and a second end pivotally secured to the other one of the two adjacent segments. Such a configuration permits each segment to be twisted relative to the two adjacent segments, causing the therapeutic toy to assume any one of an infinite number of configurations. A textured coating or other material is placed over at least a portion of the outer surface of the segments. The textured coating provides a soft, malleable surface that contacts hands and fingers.

In an alternative embodiment, a magnetic connection creates the link between adjacent segments of the therapeutic twisting hand toy. A cylindrical magnet is located on the first end face of each segment. A cylindrical central channel magnet extends into the second end face of each segment. The cylindrical central channel magnet engages the cylindrical magnet on an adjacent segment and the combination secures the plurality of segments of the therapeutic toy together. In another embodiment, the therapeutic twisting hand toy using a magnetic connection between adjacent segments is coated with a textured coating.

DETAILED DESCRIPTION OF THE INVENTION

Figure 1:
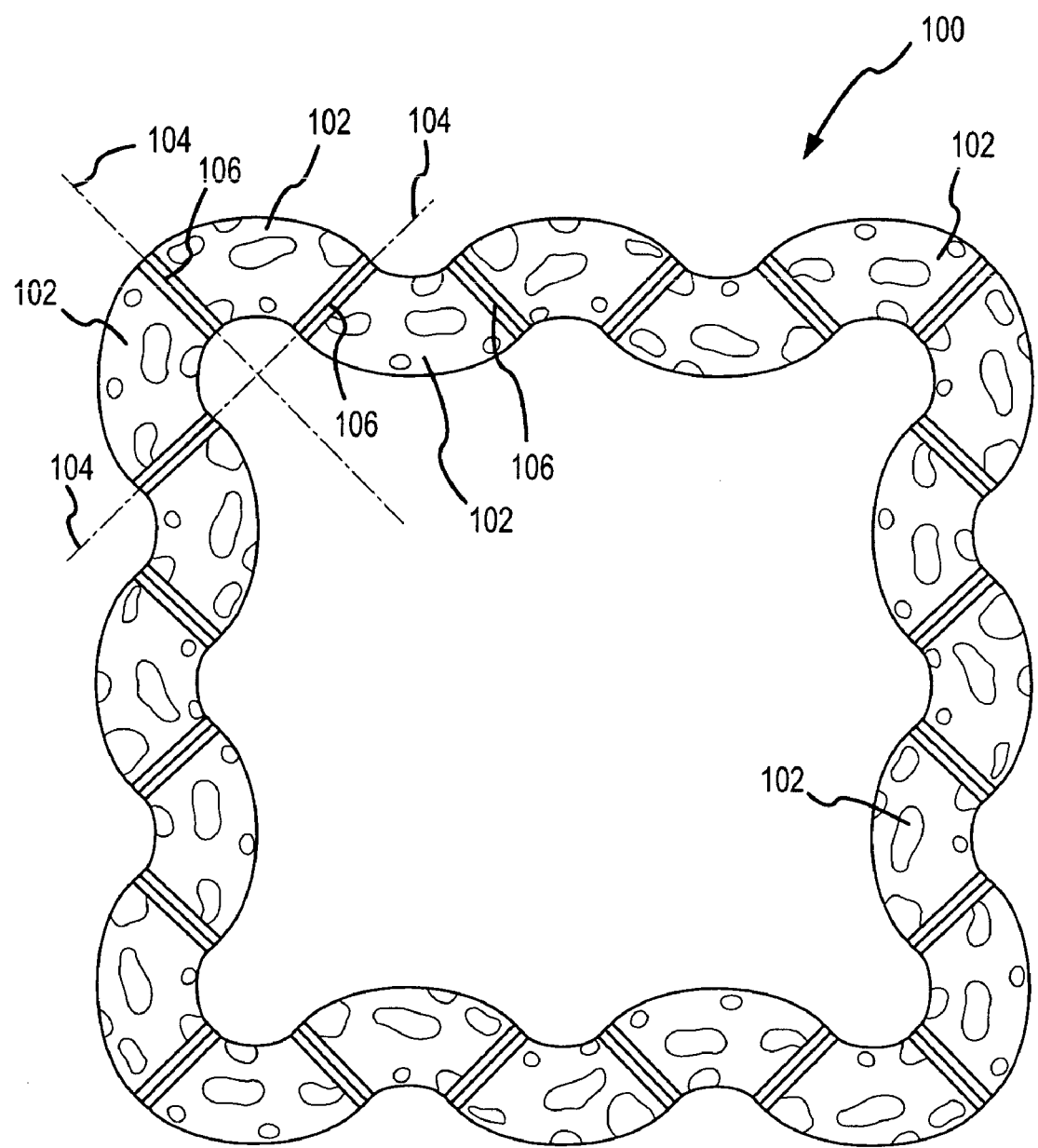
FIG. 1 illustrates a first embodiment of a therapeutic toy in accordance with the present invention.

One important aspect of the invention provides a therapeutic hand toy that can be manipulated into an infinite number of shapes and configurations. The invention is best applied to relieve minor stress as well as strengthen hand muscles, rehabilitate finger and joint movement and improve overall range of hand motion. In use, the resulting toy provides hours of use and enjoyment, thereby increasing the effectiveness of the numerous therapeutic benefits. The textured toy may be manufactured in a variety of colors, shapes, and textures that are sized for children as well as adults.

One particular advantage of the invention is applying a material, substance or device to the surface of one or more of the segments. The surface application provides a unique feel to the therapeutic toy, creating a unique sensation and feel to the user's hands and fingers. In addition, modifying the surface of the segments may reduce hand fatigue, thus allowing the user to manipulate the toy for longer periods of time. Other features include helping with smoking cessation or other habits, assisting those suffering from hand and wrist ailments, such as arthritis, carpel tunnel syndrome, and the like, and contributing to muscle tone development and hand and finger dexterity. Further, the toy may help relieve minor stresses, increase range of hand motion, improve muscle performance and rehabilitate hand muscles and joints. Also, substances, textures or temperature variations may be provided directly to the user's hands and fingers. Hence, the toy facilitates hand, mind and overall well being.

A wide variety of materials or devices may be associated with the therapeutic hand toy segments to provide various healing and restorative effects. As one example, various coatings or coverings may be provided on the surface of the segments. The coatings or coverings may have various levels of rigidity, firmness, flexibility, softness, pliability, textures and the like. For instance, the covering may comprise a resilient material, such as rubber, foam, sponge, elastomer, urethane or similar material. These pliant materials may have a wide range of firmness levels, such as an IFD, to provide the toy with different "feel" based on the covering. Another approach to varying the firmness of the toy segment utilizes a covering that includes an encapsulated gel or liquid. The covering may also be a malleable material, such as clay, putty or playdough.

The individual toy segments may incorporate a variety of textures. For example, the segment surface may include various knobs, detents, bumps, ridges, ribs or the like that provide a distinct sensation as the user runs their fingers across the surface of the toy. Other textures include bendable or flexible tabs, extensions, posts, rubber spikes or the like. The segments may also include raised or recessed images, such as letters, characters, numbers, brail or the like. As a further example, the surface may be rough, smooth, slippery, tacky, sticky, lubricated or the like.

In a further aspect, the toy segments may include various natural or synthetic materials. For instance, the surface could include seeds, dried fruits or plants, feathers, leather, wood grains, fibers, hairs or the like. The surface may also include scented materials useful in aromatherapy, such as herbs, flowers or even flavored substances.

The toy segments may also include materials such as lotions, oils, ointments or lubricants that may be transferred to the user's hands. In some cases, the toy segments may include a medicament that contacts the user's hands, such as an arthritis ointment, medicated hand cream, antibiotic or the like.

In other embodiments, various moveable, slidable, depressible or rotatable elements or devices may be arranged on or about individual toy segments. As one example, a rotatable sleeve or cylinder may be placed about the segments. As another example, a segment may include slidable tabs or other elements that move horizontally or vertically relative to the surface of the toy segment. In still another example, a toy segment may include depressible tabs or buttons disposed on the surface of the segment.

The toy segments may also be configured to move in and out, such as by encasing springs on the outer surface. Also, the segments could be configured to vibrate by incorporating one or more vibratable elements on or below the surface, such as a piezoelectric, ceramic or mechanical vibrator. The segments could also be used to provide electrotherapy by producing mild electrical shocks. The electrotherapy energy may be provided by one or more batteries, either included within the segments or as an external battery pack. Also, heating or cooling elements could be provided to heat or cool the segments. Examples of heaters or coolers include Peltier devices.

Each segment that, in combination with other segments, forms the therapeutic hand toy may incorporate an identical coating or texture, dissimilar coatings or textures, or any combination thereof. For example, a twenty segment hand toy may be constructed of twenty feather coated segments. Alternatively, a twenty segment had toy may be formed by twenty individual segments, each one having a different coating and/or texture. Since any number of combinations in between is possible, the twenty segment hand toy may be manufactured using an infinite number of combinations of textured and/or coated segments.

One specific advantage of the present invention is a magnetic connector adapted for connecting adjacent segments of the therapeutic toy. The magnetic connectors are important for easily changing out or completely removing segments to create even more shapes and configurations. In addition, the magnetic connectors may provide therapeutic benefits, such as magnetic therapy to individuals suffering from arthritis.

Therapeutic Toy

Referring now to the drawings, the systems and methods of the invention will be described in detail. Referring first to FIG. 1, an example of a textured therapeutic toy in accordance with one embodiment of the present invention will be described. The toy consists of a plurality of rotatably coupled links 102 that are interchangeable with one another. The links are connected end-to-end to form a ring. The links may be constructed of wood, plastic, composites, metals or the like. Exemplary techniques for constructing such links are described in, for example, U.S. Pat. Nos. 4,509,929; 5,110,315; and 6,086,445, and in copending U.S. application Ser. No. 10/744,962, filed Dec. 23, 2003, the complete disclosure of each is herein incorporated by reference.

Figure 2:
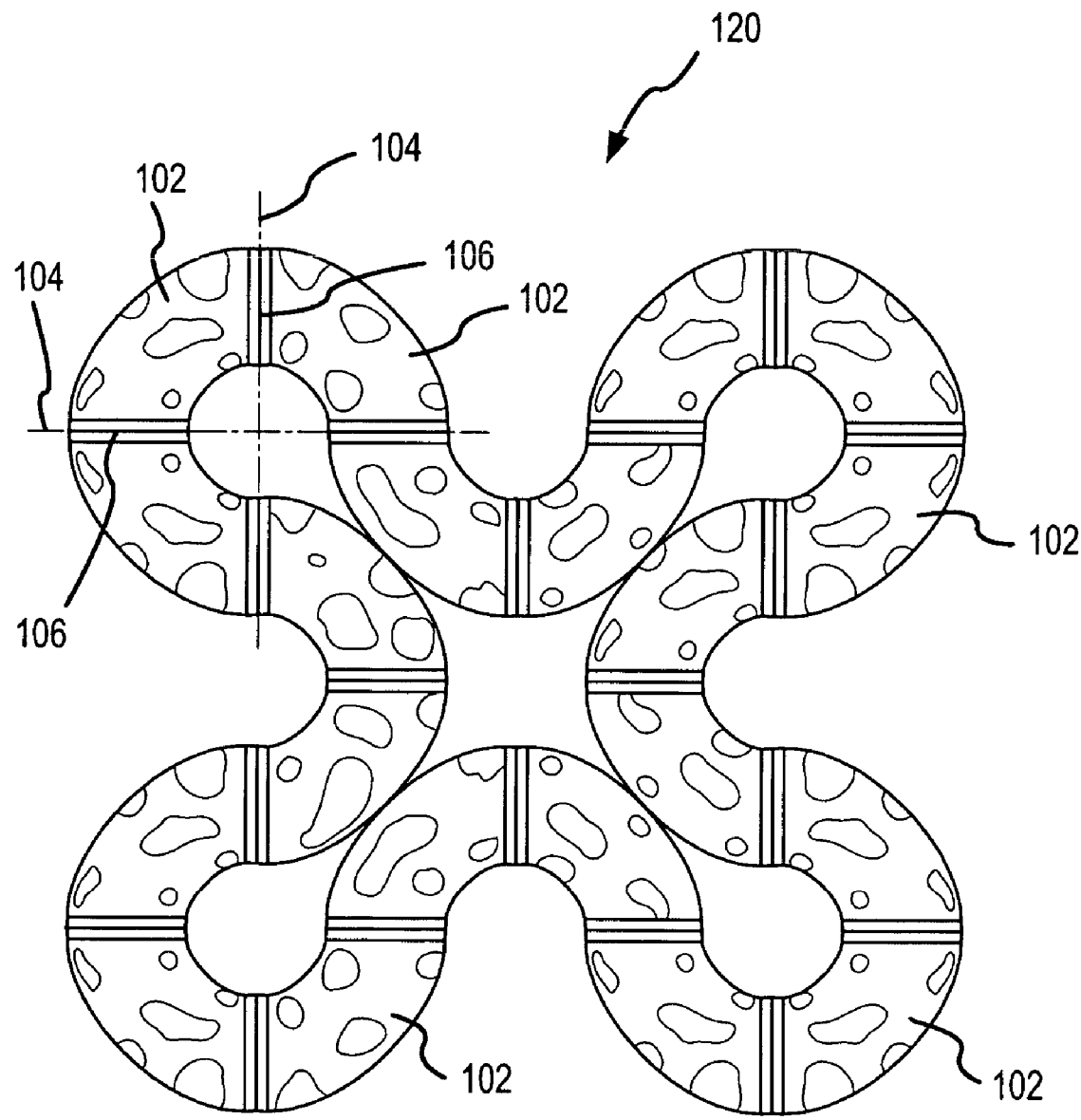
FIG. 2 illustrates a second embodiment of a therapeutic toy in accordance with the present invention.
Figure 3:
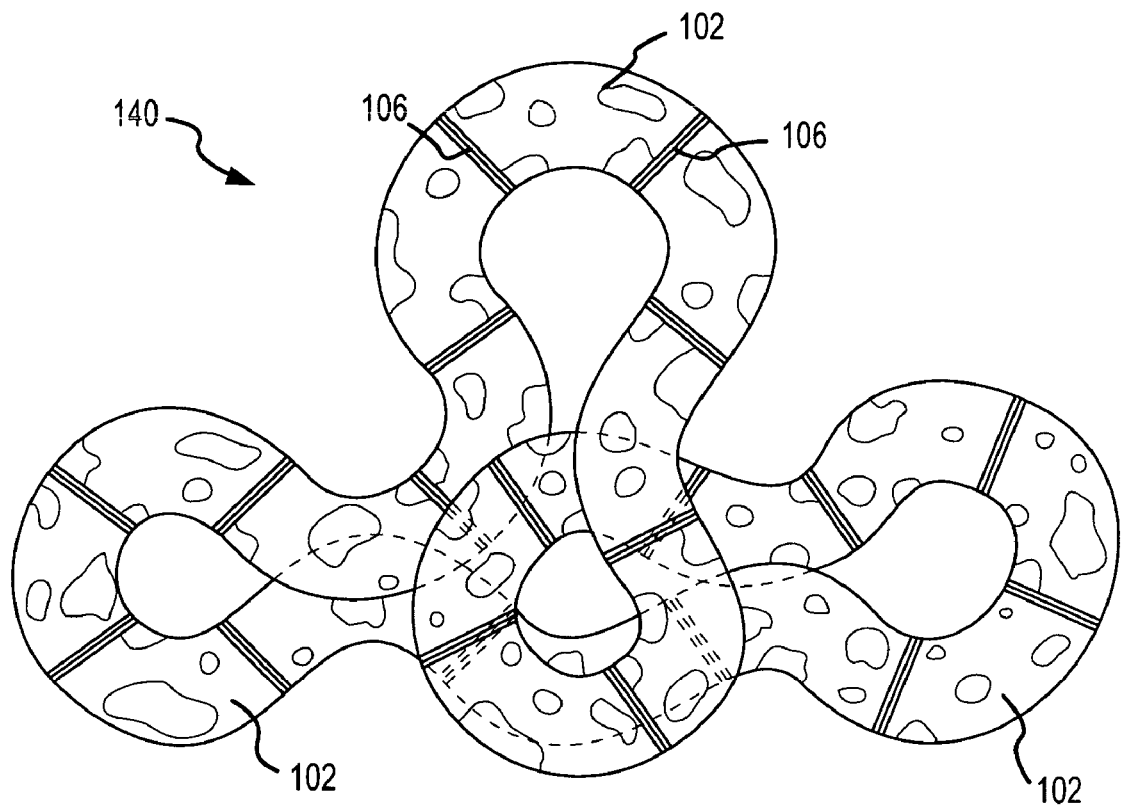
FIG. 3 illustrates a third embodiment of a therapeutic toy in accordance with the present invention.

FIG. 1 illustrates one embodiment of a textured therapeutic toy. Therapeutic toy 100 is formed by a plurality of pivotally connected segments 102, which may be twisted into an infinite variety of configurations, such as the unique and decorative clover leaf 120 shown in FIG. 2 (particularly when the toy has twenty segments) and the random design 140 shown in FIG. 3. The designs in the embodiments of FIGS. 1 and 3 have sixteen segments, which can be seen in the flat configuration shown in FIG. 1. Every segment 102 has a twisting axis 104 at each end thereof which passes through an end interface 106 between each pair of adjacent segments. Each segment may be twisted relative to either adjacent segment through 360 degrees by displacing or flipping the remainder of therapeutic toy 100.

The therapeutic toy 100 has an amazing retention property, which causes the segments thereof to remain in the last configuration set by the user. Therapeutic toy 100 is readily twistable into new configurations (See therapeutic toy 120, 140 of FIGS. 2 and 3), but tends to retain the prior configuration until retwisted. Preferably, each extension fits snugly into the cooperating channel of the adjacent segment, which aids the retention property. In addition, some configurations have points of contact between segments that touch (and with the support surface). These contact points permit mutual leaning and support, which aids in configuration retention.

Another source of retention is due to the subtle relationship between the interface twisting axes 104. Twisting axes 104 are randomly oriented. The probability of two axes being perfectly aligned or coincident in a given configuration is highly remote. Such alignments, when they do occur, offer less resistance to pivoting because they involve the snug-static friction of only the aligned interfaces. In the usual non-aligned case, more interfaces are involved, and entire sections of the therapeutic toy must be simultaneously twisted and shifted as a unit in order to move a single segment.

The torus curve along each segment body portion 102 causes the two twisting axes of each segment to be non-aligned. A single segment 102 cannot be twisted relative to both adjacent segments at the same time without displacing other segments within the therapeutic toy 100. The segments 102 cannot be displaced independently.

Typically, when the user initially twists therapeutic toy 100, the twisting axes 104 are random and non-aligned. The initial locked group includes the entire chain of segments. The force required to displace a single segment 102 must be sufficient to disturb the entire toy, simultaneously moving every segment and reorienting every twisting axis. The chain-wide disturbance proceeds until two axes come into alignment. The initial resistance to change in the therapeutic toy is the origin of the configuration retention characteristic. This initial resistance is at least, in part, responsible for the self-supporting feature of toy 100 shown in FIG. 1. Minor displacement forces (such as gravity and occasional bumps) acting on the toy are insufficient to overcome the non-alignment resistance.

Figure 4:
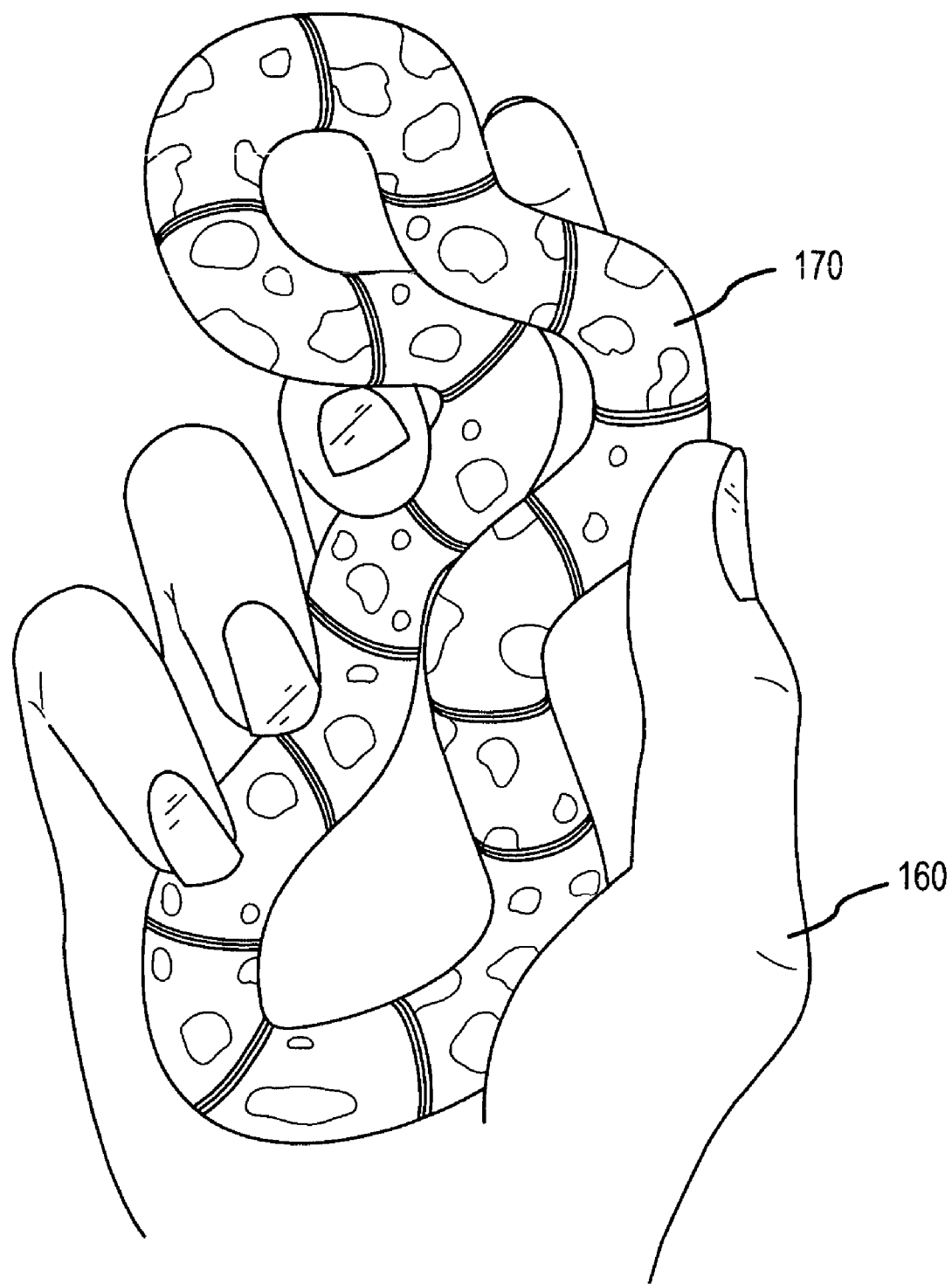
FIG. 4 illustrates use of an embodiment of a therapeutic toy in accordance with the present invention.

FIG. 4 illustrates an embodiment of a therapeutic toy 170 in operation. A user manipulates toy 170 in his/her hand 160 by twisting and turning the segments to form a unique shape or design. The twisting, turning and rotating motion of hand 160 provides strengthening for the hand and finger muscles as well as rehabilitation for the joints. Therapeutic toy 170 can also be used as a mental distraction for a person who is trying to quit smoking. For example, when a smoker is on the telephone, he/she may instinctively light up a cigarette to keep his/her hands busy. Toy 170 replaces the habitual lighting and smoking of a cigarette, and occupies a smoker's hands and brain, thus replacing the function of the cigarette.

The coatings on the links may be essentially any type of color, including translucent or transparent, and may have a variety of thicknesses, textures, durometers, compression deflection pressures, and the like. Merely by way of example, the thickness of the coating may be in the range from about 1 mm to about 6 mm, and more preferably from about 2 mm to about 4 mm. Examples of textures that may be used include dots, detents, dimples, lines, roughened, smooth, sticky, and the like.

Figure 5A:
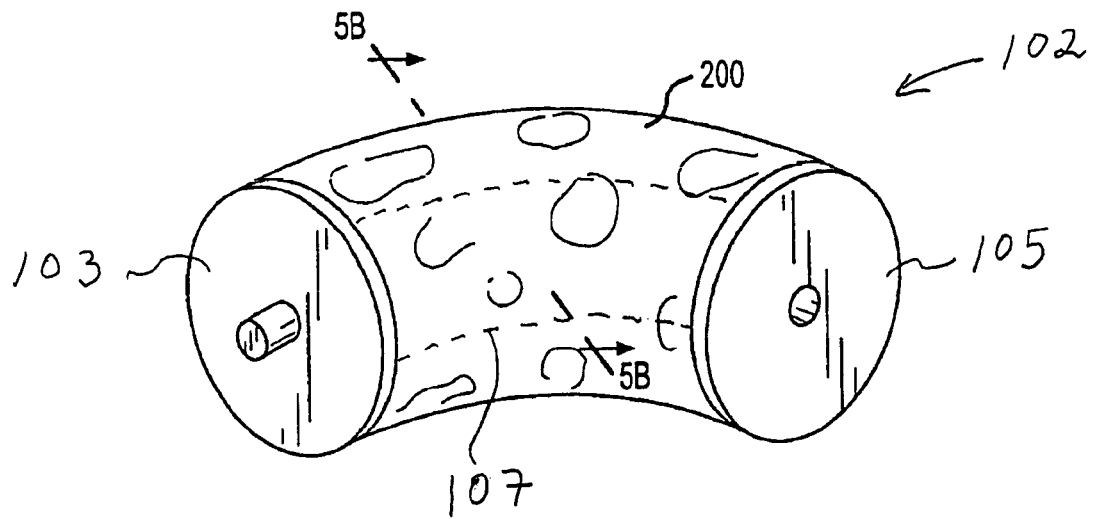
FIG. 5A illustrates a first textured coating on a single segment of a therapeutic toy in accordance with the present invention.

FIG. 5A illustrates a single textured pivotally connected segment 102 from therapeutic toy 100. Segment 102 has two ends 103 and 105 and a shaft 107 with a relatively small diameter. The ends and shaft may be constructed of a hard material, such as a hard plastic, polycarbonate, wood, metal or the like. A textured coating 200 is applied to the outer surface of segment 102 (and particularly about the shaft 107) thus providing a surface that is soft and malleable such that it creates a pleasant sensation and feel to the user's hands and fingers. In addition, the soft texturing of the surface of the segments reduces hand fatigue, thus allowing the user to manipulate the toy for longer periods of time. Textured coating 200 may be a rubber, plastic, silicone gel, composite material or the like, however, those skilled in the art will understand that any coating may be used that is consistent with the properties of the above listed coatings.

Figure 5B:
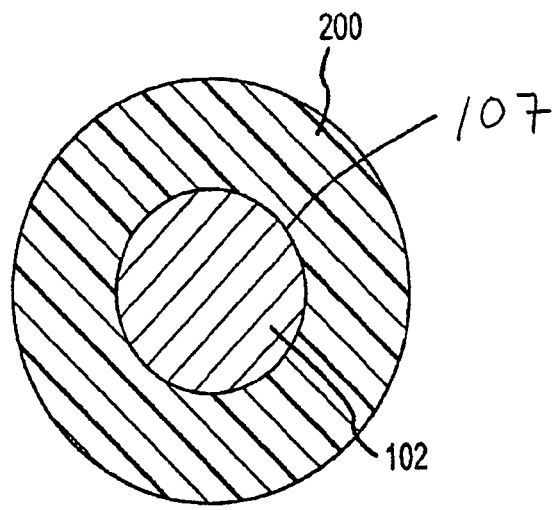
FIG. 5B is a cross-sectional view of the segment of FIG. 5A.

FIG. 5B shows the cross-sectional view of the textured coating 200 applied to the surface of textured pivotally connected segment 102 shown in FIG. 5A. In one embodiment, texture coating 200 is applied to the surface of segment 102 (and particularly shaft 107) using the process of insert molding or injection molding, however, any manufacturing process may be used that adheres a textured coating to a segment surface. First, the plastic is injected to form segment 102. Then, segment 102 is then removed from the mold. Finally, segment 102 is placed back into the mold and textured coating 200 is injected and adheres to the outer surface of segment 102. Ends 103 and 105 hold the coating in place.

Figure 6A:
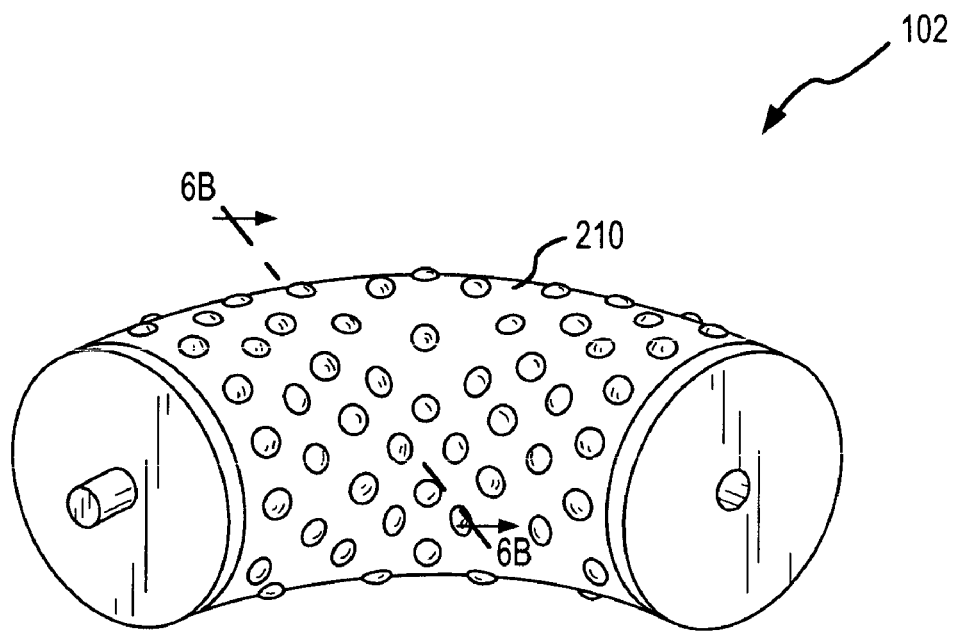
FIG. 6A illustrates a second textured coating on a single segment of a therapeutic toy in accordance with the present invention.
Figure 6B:
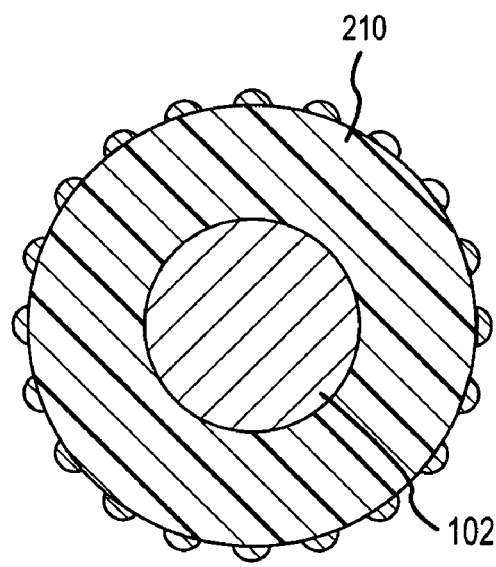
FIG. 6B is a cross-sectional view of the segment of FIG. 6A.

FIG. 6A illustrates a second embodiment of textured coating 210 with raised nodules applied to a single textured pivotally connected segment 102. FIG. 6B shows a cross sectional view of the texture coating 210 with raised nodules applied to the textured pivotally connected segment 102 shown in FIG. 6A.

Therapeutic toy 100 of FIG. 1 is formed by sixteen identical torus segments 102 connected end-to-end to form a continuous annular device. Each segment 102 is a 90-degree section of a torus, having a curved body portion, with recessed face at one end and recessed face at the other end.

Figure 7:
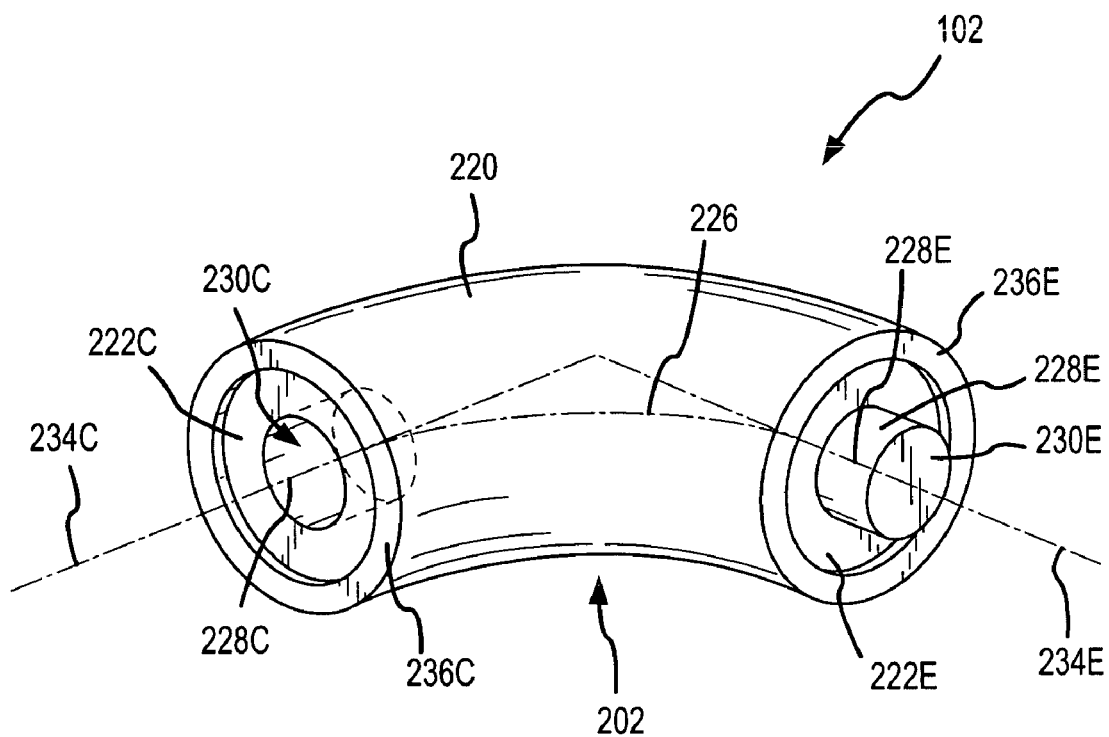
FIG. 7 illustrates a single segment of a therapeutic toy having connectors for adjoining adjacent segments of the therapeutic toy in accordance with the present invention.

FIG. 7 illustrates another embodiment of a single segment 202 that may have a coating added to it. In describing segment 202, it will be appreciated that segment 102 is similar in many respects. Centerline of symmetry of curved segment 202 is a 90-degree arc defining the plane of the torus segment. Centerline 226 has end points 228E and 228C. Each end face 222 defines an interface plane containing end points 228, and which is perpendicular to center line 226 at end points 228, and perpendicular to the plane of the torus segment. The interface planes are also perpendicular to each other in the 90-degree embodiment of FIG. 7.

End face 222E of each segment has a schematically shown central extension 230E, with a straight central axis 234E extending perpendicular to the interface plane. Axis 234E is tangent to curved centerline 22 at end point 228E thereof. End face 222C of each segment has a cooperating cylindrical central channel 230C with a central axis 234C extending perpendicular to the interface plane. Axis 234C is tangent to curved centerline 226 at one end point 228C thereof.

The central channel of each torus segment in the annular device has an inwardly tapering rib at its terminal portion located distally from end face 222C so as to receive the central extension-channel interface which locks a distal bulb portion of the central extension beyond the terminal portion of the central channel. Center axis 234E and 234C of each interface coincide defining a common pivoting or twisting axis. Multiple segments may be twisted into an infinite number of random configurations, each of which has a continuous closed centerline of symmetry formed by centerline 226 through each segment. End points 228 of adjacent centerlines remain coincident regardless of the complexity of the configuration of the annular device.

End faces 222 have raised peripheral rims 236E and 236C, which abut with an identical cooperating peripheral rim on the adjacent segment. Rims 236 are circular and define the common interface plane therebetween.

Figure 8:
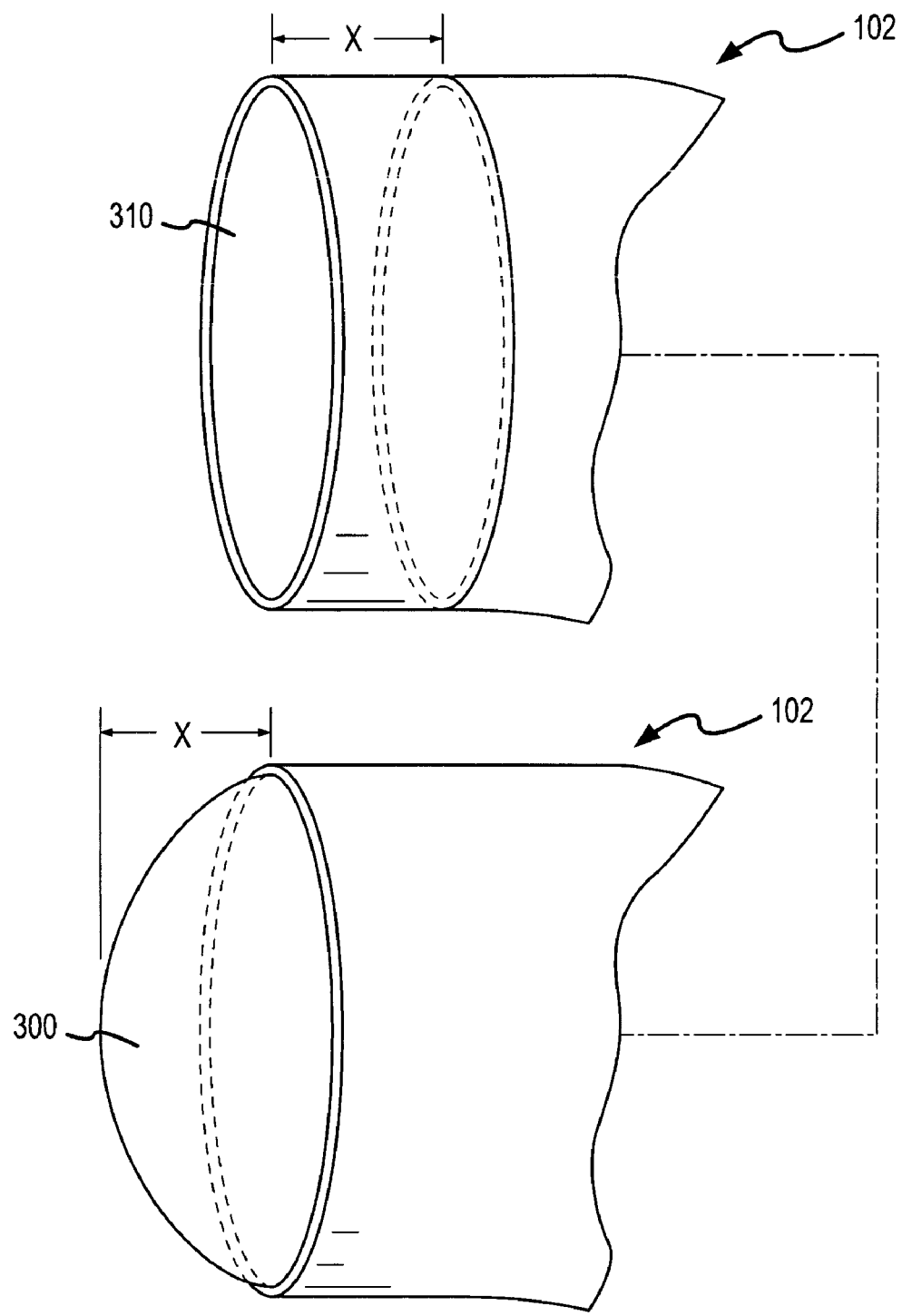
FIG. 8 illustrates one embodiment of a magnetic connector for connecting adjacent segments of a therapeutic toy in accordance with the present invention.

FIG. 8 illustrates a first embodiment of a magnetic connection for adjoining adjacent segments 102' of a therapeutic toy (having any of the coatings described herein) in accordance with the present invention. The magnetic connection is achieved using two opposing pole magnets 300, 310 that fit together to connect adjacent segments. The first magnet 300 is a spherical magnet on the first end face of segment 102. The second magnet is a cylindrical central channel magnet extending into the second end face of segment 102 for engaging spherical magnet 300 on the other one of the two adjacent segments for securing the plurality of segments together. Spherical magnet 300 and cylindrical channel magnet 310 are of a length X such that spherical magnet 300 fits securely into cylindrical channel magnet 310 and creates the connection between adjacent segments of therapeutic toy 100.

Figure 9A:
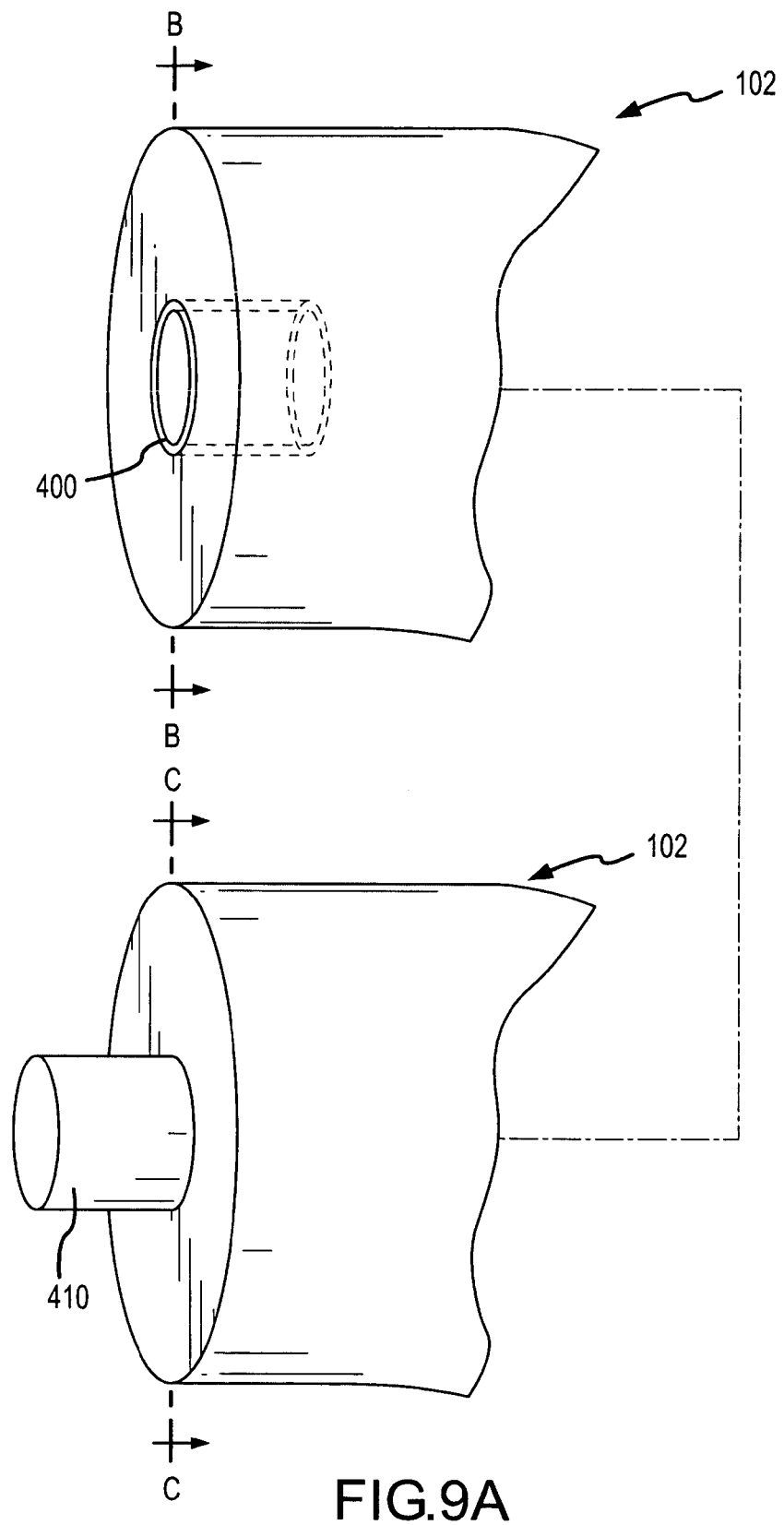
FIG. 9A illustrates a second embodiment of a magnetic connector for connecting adjacent segments of a therapeutic toy in accordance with the present invention.
Figure 9B:
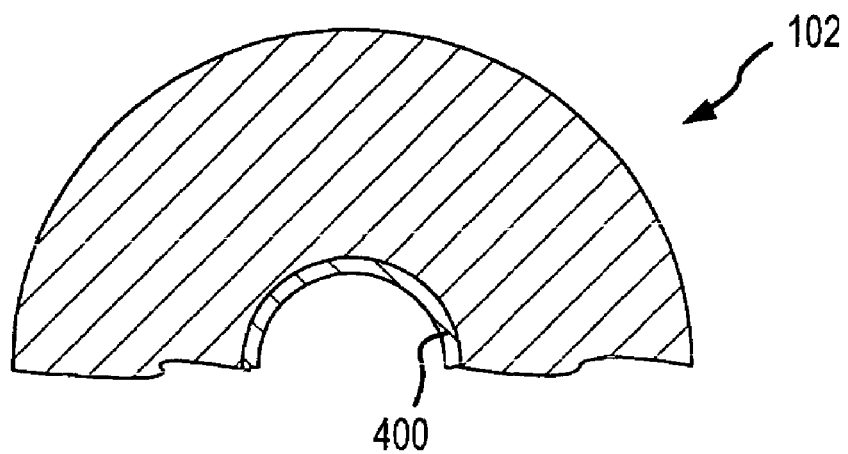
FIGS. 9B and 9C illustrate the cross sections of the second embodiment of a magnetic connector shown in FIG. 9A.
Figure 9C:
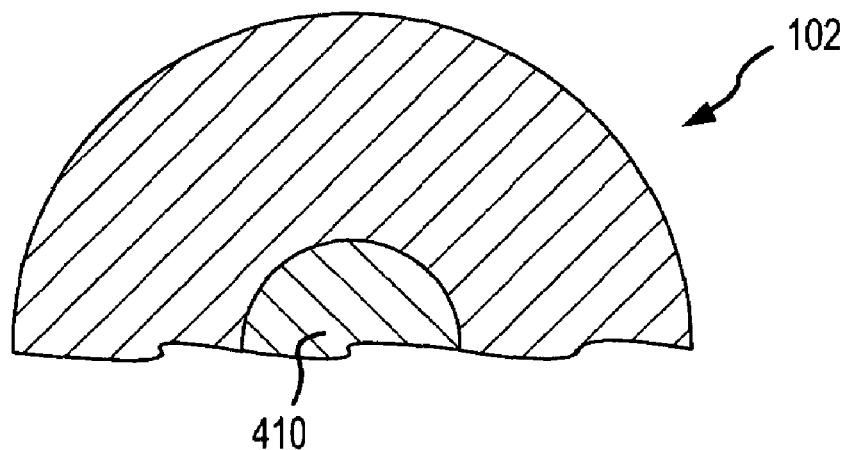

FIG. 9A illustrates a second embodiment of a magnetic connection for adjoining adjacent segments 102" of a therapeutic toy (including those having coatings) in accordance with the present invention. The magnetic connection of the second embodiment is also achieved using opposing pole magnets 400, 410. The first magnet is a cylindrical magnet 410 on a first end face of segment 102". The second magnet is a cylindrical central channel magnet 400 extending into the second end face of segment 102" for engaging cylindrical magnet 410 on the other one of the two adjacent segments for securing the plurality of segments together. FIGS. 9B and 9B illustrate the cross sections of the second embodiment of a magnetic connection shown in FIG. 9A.

Figure 10:
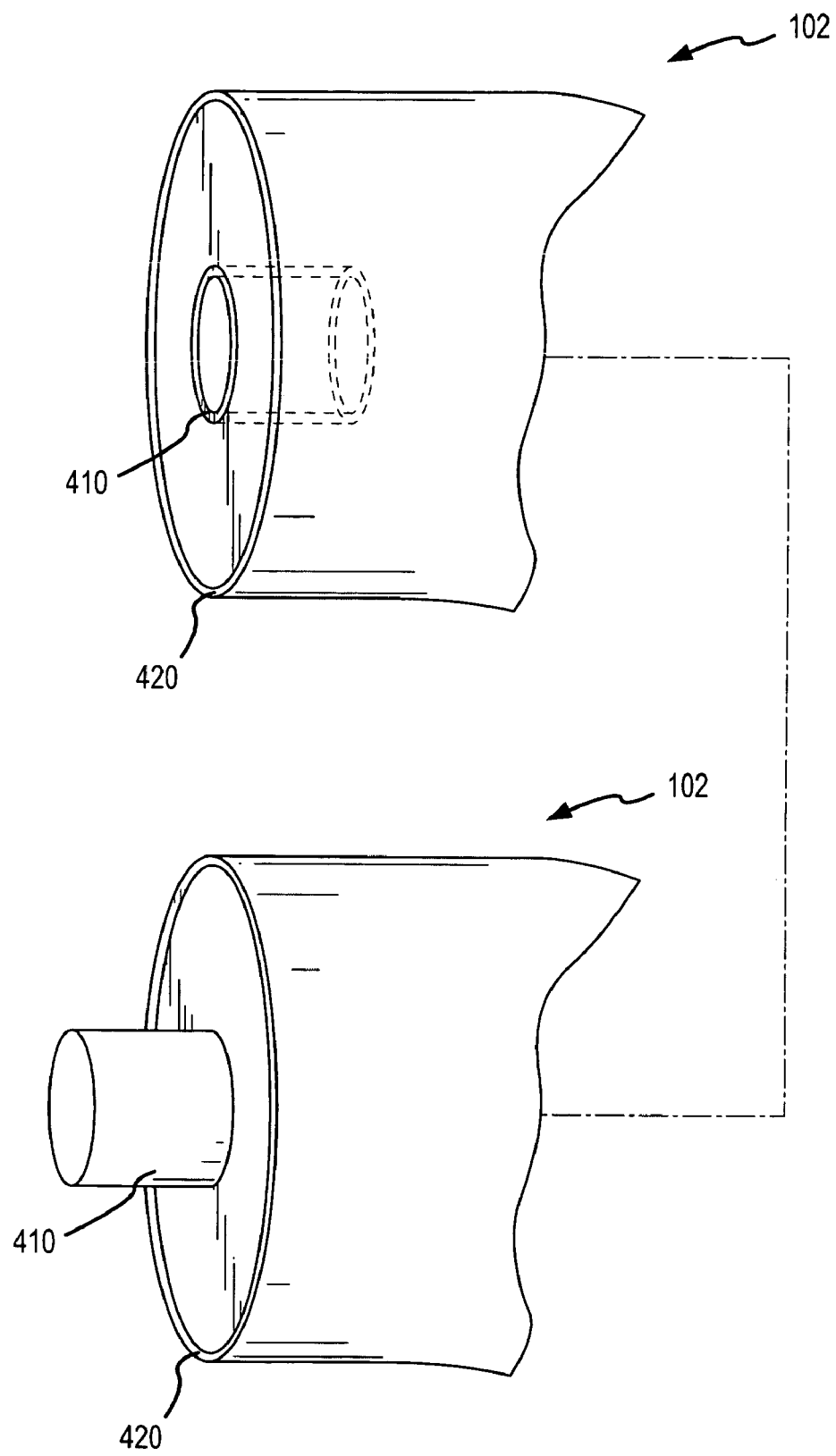
FIG. 10 is a magnetic connector with a textured coating applied to the outer surface of a segment.

FIG. 10 is a magnetic connection using a cylindrical magnet 410a on a first end face of a segment 102a and a cylindrical central channel magnet 400a extending into the second end face of segment 102a. Segment 102a has a textured coating 420 applied to the outer surface of the segment. Textured coating may be a rubber, plastic, silicone gel, composite material or the like, however, those skilled in the art will understand that any coating may be used that is consistent with the properties of the above listed coatings. Further, any of the coatings described herein may be used with any of the segments 102', 102" or 102a.

Segment Coatings, Textures and Features

Figure 11:
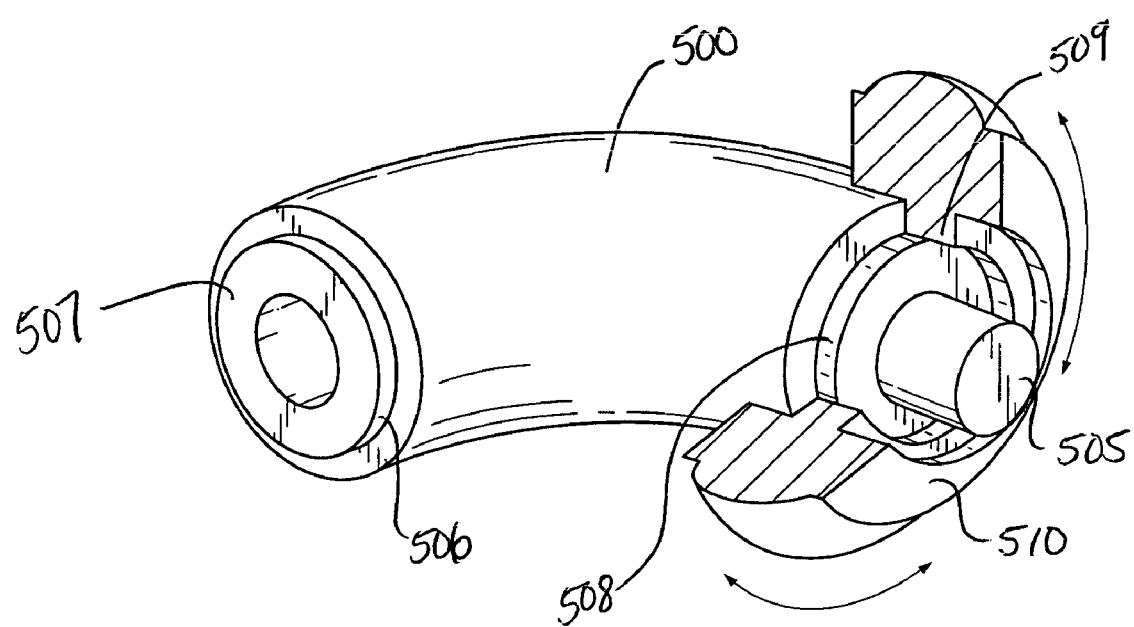
FIG. 11 illustrates a single segment of a therapeutic toy having a moveable element provided on the segment.

FIG. 11 illustrates an individual segment 500 having a rotatable element 510 disposed on the surface of segment 500 closest to a central extension-channel interface 505. A cooperating cylindrical central channel 507 of an adjacent segment receives central extension-channel interface 505 and secures rotatable element 510. A rotatable element rib 509 rests on central channel lip 507 and a central extension-channel lip 508 on an adjacent segment allowing rotation in a clockwise or counterclockwise direction about segment 500. Rotatable element 510 may be positioned at other locations on segment 500, and multiple elements 510 could be placed in the same segment. Also, some segments may include element 500 while others do not. In some cases, element 510 could be slid transversely along segment 500. Also, segment 500 as well as other segments described herein may be coupled to adjacent segments using a variety of different connections.

Figure 12:
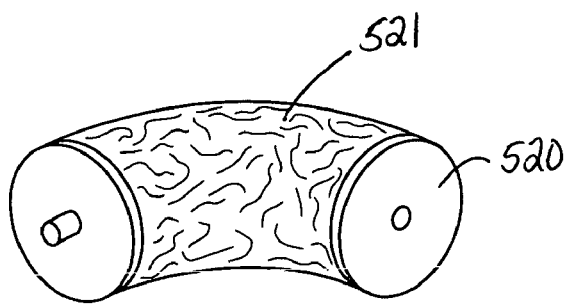
FIG. 12 illustrates a medicinal or ointment coating on a single segment of a therapeutic toy in accordance with the present invention.
Figure 13:
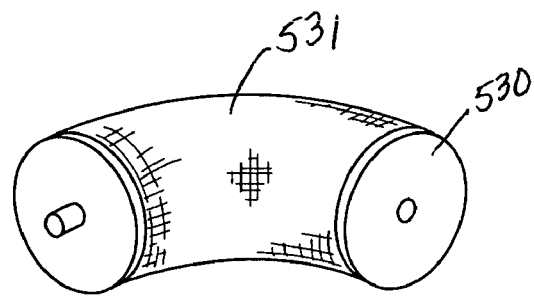
FIG. 13 illustrates a fabric coating on a single segment of a therapeutic toy in accordance with the present invention.
Figure 14:
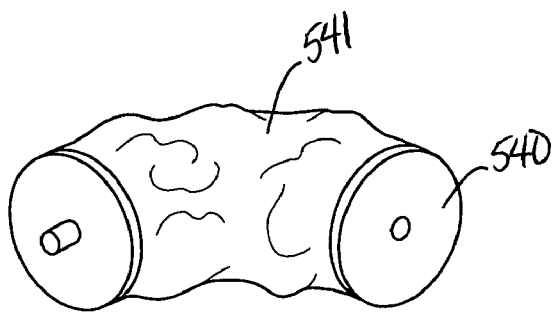
FIG. 14 illustrates a playdough coating on a single segment of a therapeutic toy in accordance with the present invention.
Figure 15:
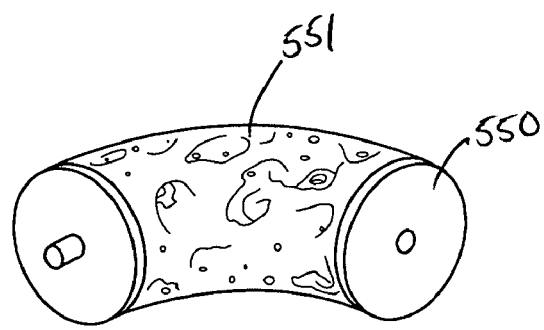
FIG. 15 illustrates a sponge coating on a single segment of a therapeutic toy in accordance with the present invention.

FIGS. 12-15 illustrate individual segments having a coating or covering disposed about the segment. FIG. 12 shows segment 520 having a medicine, ointment, cream, lubricant or similar content disposed on the surface. In operation, when the user handles the hand toy, the contents from the surface are released onto the user's hands. FIG. 13 illustrates a segment 530 with a fabric coating 531. The fabric coating can be a material, mesh, cotton, wool, silk, fleece, spandex, linen, denim or similar material. The fabric coating 531 provides a unique sensation to the user's touch and increases the amount of time the user will operate the therapeutic hand toy. FIG. 14 illustrates a segment 540 with playdough 541 on the surface of the segment. Playdough 541 can be any malleable material such as putty, clay, or similar material. In operation, kids as well as adults will enjoy the soft, supple and pliable feature of the coating material, which translates into hours of enjoyment. FIG. 15 illustrates a segment 550 with a sponge covering 551. Sponge covering 551 may be any soft, springy and squishy covering such as foam or similar material. The distinctive nature of sponge covering 551 provides hours of pleasure to both adults and children.

Figure 16:
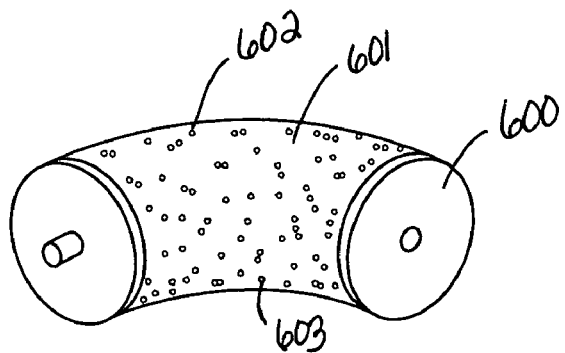
FIG. 16 illustrates a seeded coating on a single segment of a therapeutic toy in accordance with the present invention.
Figure 17:
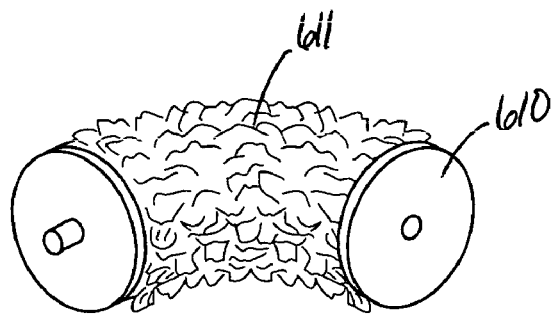
FIG. 17 illustrates a feather coating on a single segment of a therapeutic toy in accordance with the present invention.
Figure 18:
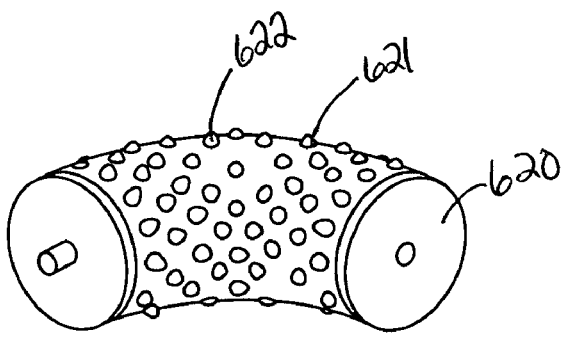
FIG. 18 illustrates a coating of spikes on a single segment of a therapeutic toy in accordance with the present invention.
Figure 19:
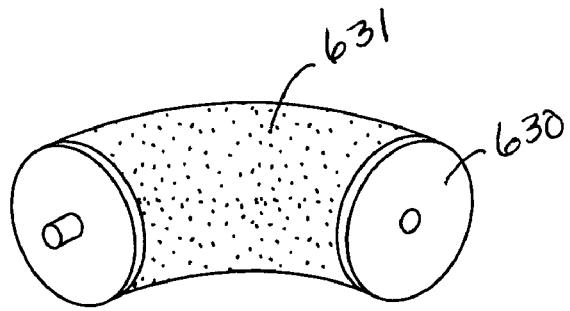
FIG. 19 illustrates a sandpaper coating on a single segment of a therapeutic toy in accordance with the present invention.

FIGS. 16-19 illustrate individual segments having a unique texture disposed on the surface of the segment. FIG. 16 shows segment 600 with a plurality of seeds 601, 602, 603 disposed on the surface of segment 600. FIG. 17 illustrates segment 610 having a surface of feathers 611. The feather texture coating 611 can also be manufactured of a natural fiber, a synthetic fiber, animal hair or similar texture. FIG. 18 shows segment 620 with a plurality of rubber spikes 621, 622 disposed on the surface. Rubber spikes 621, 622 may also be knobs, detents, bumps, ridges, ribs, bendable or flexible tabs, extensions, posts or similar textures. FIG. 19 illustrates segment 630 having a surface of sandpaper 631. Sandpaper texture 631 may also be manufactured of a texture having a rough, smooth, slippery, tacky, sticky, or lubricated sensation on the user's hands and fingers.

Figure 20:
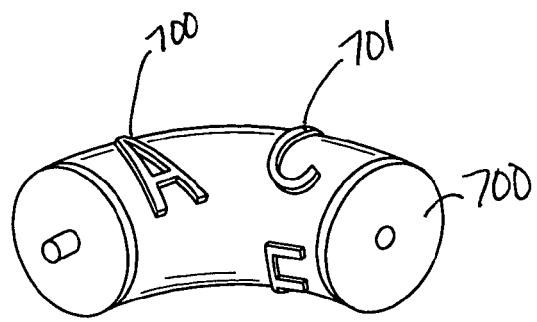
FIG. 20 illustrates a coating of raised characters on a single segment of a therapeutic toy in accordance with the present invention.
Figure 21:
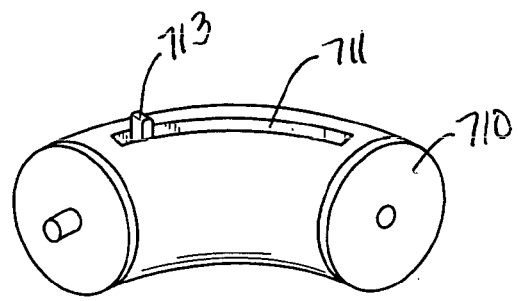
FIG. 21 illustrates a slidable tab integrated into and disposed on the surface of a single segment of a therapeutic toy in accordance with the present invention.
Figure 22:
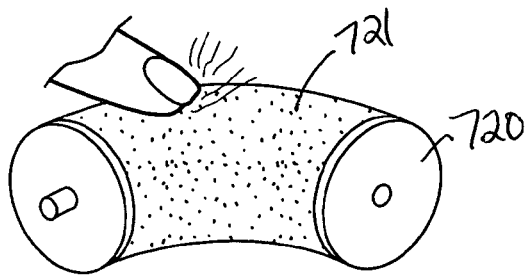
FIG. 22 illustrates a scratch and sniff coating on a single segment of a therapeutic toy in accordance with the present invention.
Figure 23:
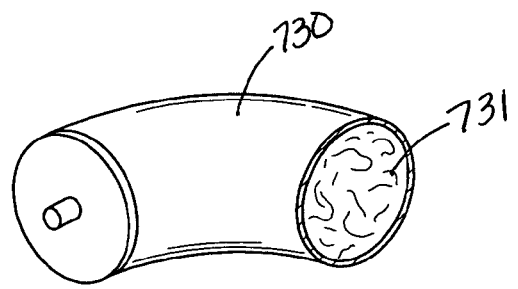
FIG. 23 illustrates a gel-filled single segment of a therapeutic toy in accordance with the present invention.

FIGS. 20-23 show several coatings, textures and segment properties on individual segments. FIG. 20 illustrates individual segment 700 having raised characters 701, 702. Raised characters 701, 702 may also be raised or recessed images, such as letters, characters, numbers, brail or the like. FIG. 21 shows an individual segment 710 having a slidable tab 713 operable in channel 711. FIG. 22 illustrates an individual segment 720 with a coating of a scratch and sniff element 721. Scratch and sniff element may also include scented materials useful in aromatherapy, such as herbs, flowers or even flavored substances. FIG. 23 illustrates an individual segment 730 having a gel filled center 731.

Figure 24:
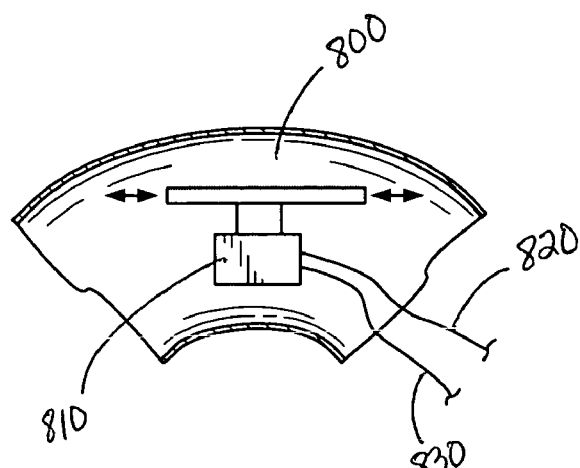
FIG. 24 illustrates a vibrating single segment of a therapeutic toy in accordance with the present invention.

FIG. 24 shows a cross section of individual segment 800 capable of providing a vibrating sensation to the user of the therapeutic hand toy manufactured from a plurality of segments 800. Segment 800 has a vibrating element 810 disposed beneath or on the surface of element 800 that provides a vibrating sensation to the surface of the element. Vibrating element 810 has a pair of leads 820, 830 that provide power to element 810. Leads 820, 830 may be coupled to a battery that is internal to the segment or a battery pack external to the segment. Leads 830, 840 may also be coupled in series or parallel with leads from other segments prior to coupling to the battery. Vibrating element 810 can be manufactured from any appropriate vibrating mechanism capable of providing vibration to the surface of a small segment 800, such as a piezoelectric vibrating mechanism, a mechanical vibrator or the like.

Figure 25:
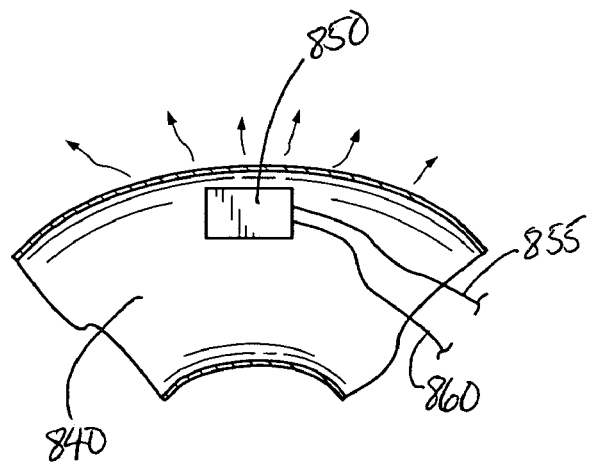
FIG. 25 illustrates a single segment having a heating/cooling device of a therapeutic toy in accordance with the present invention.

FIG. 25 illustrates a cross section of individual segment 840 capable of providing a heat or cold sensation to the surface of the segment and ultimately to the hand of the user of a therapeutic hand toy manufactured from a plurality of individual segments 840. Segment 840 has a heating and/or cooling element 850 disposed below or on the surface of element 840. Heating and/or cooling element 850 has a pair of leads 855, 860 that provide power to element 850. Leads 855, 860 may be coupled to a battery that is internal to the segment or a battery pack external to the segment. Leads 855, 860 may also be coupled in series or parallel with leads from other segments prior to coupling to the battery. Heating and/or cooling element 850 can be manufactured from any appropriate heating or cooling mechanism capable of providing a hot or cold sensation to the surface of a small segment 850, such as a Peltier device. Element 850 may also comprise a Peltier device that provides both a hot or cold sensation to the surface of segment 840, preferably by operation of a switch either on the surface of the therapeutic hand toy or on an external battery pack.

In the foregoing specification, the invention has been described with reference to a specific exemplary embodiment thereof. It will be evident that various modifications and changes may be made thereunto without departing from the broader spirit and scope of the invention as set forth in the appended claims. For example, various programming languages and techniques can be used to implement the disclosed invention. In addition, the specific logic presented to accomplish tasks within the present invention may be modified without departing from the scope of the invention. Many such changes or modifications will be readily apparent to one of ordinary skill in the art. The specification and drawings are, accordingly, to be regarded in an illustrative rather than a restrictive sense, the invention being limited only by the provided claims.

What is claimed is:

1. A therapeutic hand toy comprising:
    a plurality of serially connected rigid segments having a first end pivotally secured to one of two adjacent segments, and a second end pivotally secured to the other one of the two adjacent segments, permitting each segment to be twisted relative to the two adjacent segments causing the hand toy to assume any one of an infinite number of configurations, wherein each segment further comprises a shaft extending between the first and second ends, wherein the first and second ends extend radially away from the shaft; and
    at least one therapeutic element disposed about the shaft of at least some of the segments to provide a therapeutic treatment to a user;
    wherein each of the first and second ends has a diameter and defines a plane perpendicular to a centerline of the segment, respectively;
    wherein the shaft has a diameter that is smaller than the first and second end diameters; and
    wherein the therapeutic element comprises an elastomer material, abuts the first and second end planes, and is held in place by the first end and the second end.

2. A toy as in claim 1, wherein the therapeutic element is selected from a group consisting of resilient materials, textured surfaces, heating elements, cooling elements, vibratable elements, malleable materials, natural materials, synthetic materials, and magnets.

3. A toy as in claim 1, wherein the therapeutic element comprises a textured rubber coating on the outer surface.

4. A toy as in claim 1, wherein the plurality of segments comprises twenty segments.

5. A toy as in claim 1, wherein the plurality of segments comprises less than twenty segments.

6. A toy as in claim 1, wherein the plurality of segments comprises more than twenty segments.

7. A toy as in claim 1, wherein the diameter of each of the plurality of segments ranges between about 0.5 cm to about 3 cm.

8. A therapeutic hand toy comprising:
    a plurality of rigid segments that each comprise a shaft, a first end, and a second end, wherein the first and second ends extend radially outward from the shaft, and wherein the first end is pivotally secured to one of two adjacent segments, and the second end is pivotally secured to the other one of the two adjacent segments, permitting each segment to be twisted relative to the two adjacent segments causing the hand toy to assume any one of an infinite number of configurations; and
    a flexible elastomer material disposed about the shaft of a segment so as to be generally flush with the first and second ends, wherein the flexible material is held in place by the first and second ends of the segment,
    wherein each of the first and second ends has a diameter and defines a plane perpendicular to a centerline of the segment, respectively;
    wherein the shaft has a diameter that is smaller than the first and second end diameters; and wherein the flexible elastomer material abuts the first and second end planes.

9. A toy as in claim 8, wherein the first and second ends are circular in diameter.

10. A toy as in claim 1, wherein each segment has a twisting axis at each of the two ends, wherein each twisting axis defines an end interface between the two adjacent segments, wherein the two adjacent segments are rotatably interlocked to one another at the end interface, to thereby allow at least 360 degrees of rotation, such that centerline symmetry is maintained at the end interface between the two adjacent segments.

11. A toy as in claim 8, wherein each segment has a twisting axis at each of the two ends, wherein each twisting axis defines an end interface between the two adjacent segments, wherein the two adjacent segments are rotatably interlocked to one another at the end interface, to thereby allow at least 360 degrees of rotation, such that centerline symmetry is maintained at the end interface between the two adjacent segments.

12. A toy as in claim 1, wherein the first end is pivotally secured to the one adjacent segment at a first interface plane, and the first end extends radially away from a first central axis that extends perpendicular to the first interface plane, and wherein the second end is pivotally secured to the other adjacent segment at a second interface plane, and the second end extends radially away from a second central axis that extends perpendicular to the second interface plane.

13. A toy as in claim 8, wherein the first end is pivotally secured to the one adjacent segment at a first interface plane, and the first end extends radially away from a first central axis that extends perpendicular to the first interface plane, and wherein the second end is pivotally secured to the other adjacent segment at a second interface plane, and the second end extends radially away from a second central axis that extends perpendicular to the second interface plane.

* * * * *